United States Patent [19]

Gomyo et al.

[11] Patent Number: 4,989,455
[45] Date of Patent: Feb. 5, 1991

[54] VIBRATOR

[75] Inventors: Yasutaka Gomyo; Akira Ito; Toshiyuki Ishisaka; Tetsurou Miwa; Satoshi Hosokawa, all of Toyama; Toshio Fujimori, Tokyo; Hiroshi Ando, Tokyo; Seiichi Akizuki, Tokyo; Katsutoshi Yamaguchi, Tokyo, all of Japan

[73] Assignees: Kabushiki Kaisha Fujikoshi, Toyama, Japan; Nissan Motor Sales Co., Ltd., Tokyo, Japan

[21] Appl. No.: 381,284

[22] Filed: Jul. 18, 1989

[30] Foreign Application Priority Data

May 24, 1988 [JP] Japan .................. 1-59177[U]
Jul. 23, 1988 [JP] Japan .................. 63-97485[U]
Aug. 2, 1988 [JP] Japan .................. 63-102474[U]
Sep. 29, 1988 [JP] Japan .................. 63-126365[U]

[51] Int. Cl.$^5$ ............................................. G01M 5/00
[52] U.S. Cl. ............................................. 73/669
[58] Field of Search ............... 73/669, 665, 663, 662, 73/118.1

[56] References Cited

U.S. PATENT DOCUMENTS 2,274,619  2/1942  Swan ............................................. 73/669
3,916,677  11/1975  Isley et al. ...................................... 73/669
4,768,374  9/1988  Fouchey ......................................... 73/669

FOREIGN PATENT DOCUMENTS 43-11746  5/1943  Japan .
56-106211  8/1981  Japan .
56-39764  9/1981  Japan .

Primary Examiner—Hezron E. Williams
Assistant Examiner—Louis M. Arana
Attorney, Agent, or Firm—Wenderoth, Lind & Ponack

[57] ABSTRACT

A vibrator has a hydraulic circuit connected with a hydraulic power unit. An electromagnetic valve disposed at the hydraulic circuit is regulated for the time for actuating a switch valve through a control signal. A plunger capable of bearing a load of an object to be tested at an upper end portion thereof has an oil chamber for pressurizing the plunger in such a manner as to be able to move upward and downward. An oil passage communicates with the oil chamber and with the electromagnetic valve. A vibration applying cylinder is capable of vibrating the plunger at a desired amplitude and frequency through hydraulic oil which is fed from the electromagnetic valve. A lift means lifts the vibration applying cylinder to a predetermined height. A controller capable of outputting, as a control signal, a setting signal for setting at least the amplitude and frequency of the plunger is provided. A control unit actuates the hydraulic power unit and the electromagnetic valve in accordance with the control signal.

25 Claims, 13 Drawing Sheets

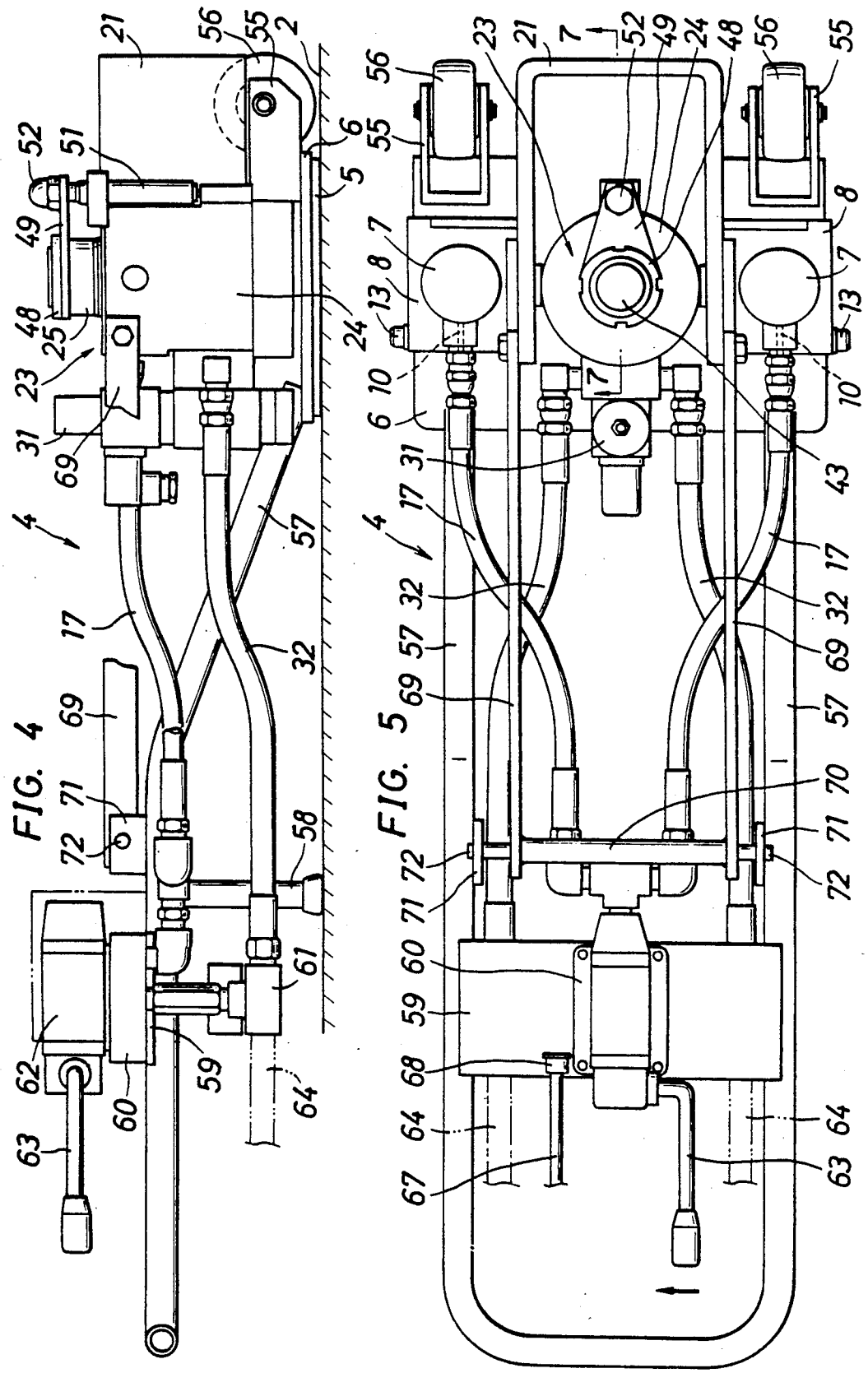

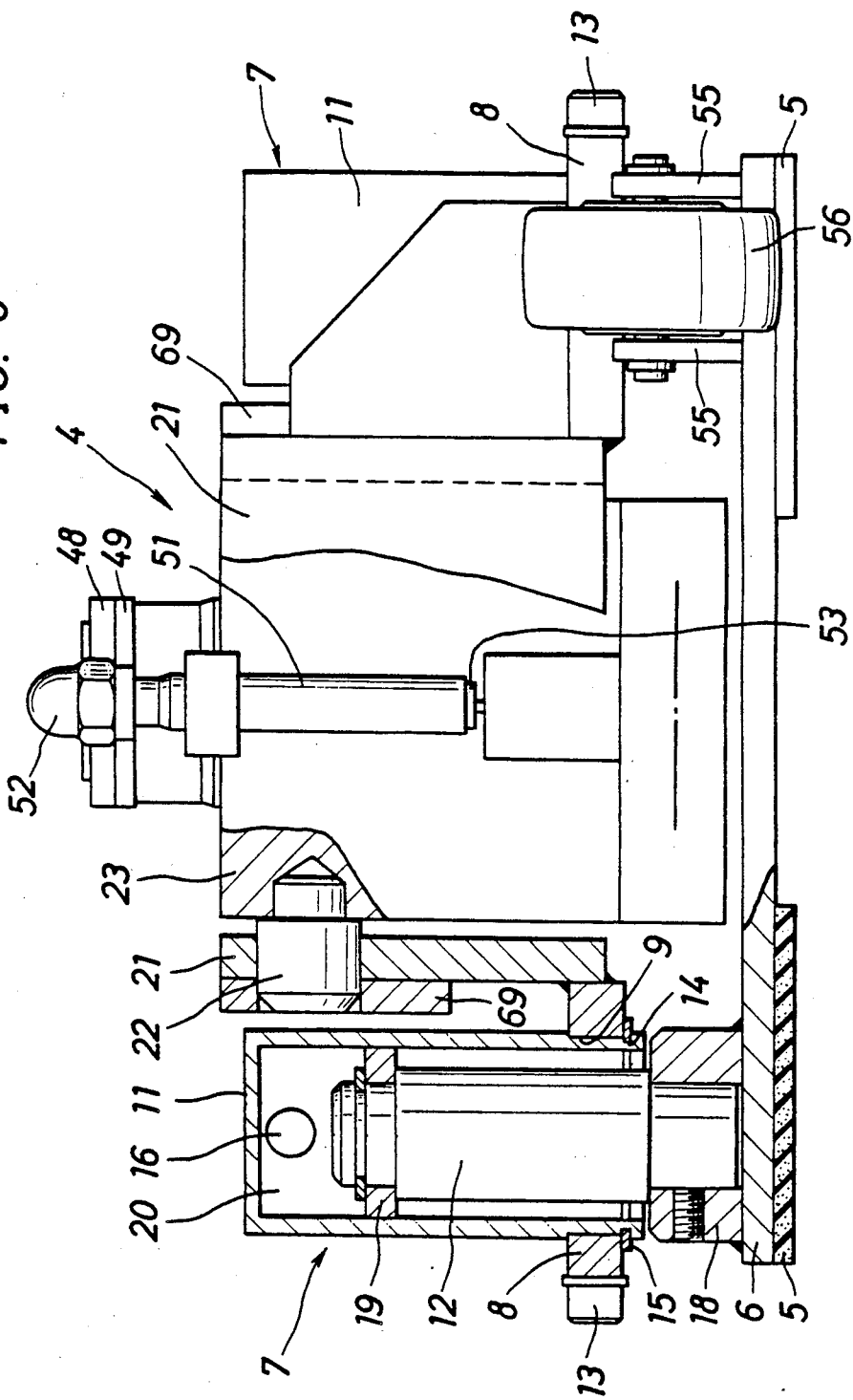

VIBRATOR

FIELD OF THE INVENTION

This invention relates to a vibration applying device (hereinafter simply referred to as the "vibrator") which is capable of identifying an unusual noise, such as a squeaking noise of a vehicle body, a rattling noise of interior equipment of a vehicle, etc. and accurately locating a place that generates such unusual noise.

DESCRIPTION OF THE PRIOR ART

For example, when a car is running, there sometimes occur such unusual noises as squeaking or rattling, generated from a poorly spot welded part of its body or loosened interior equipment of the car, which are chiefly caused by an inferior structure or assembling technique of the car. These noises naturally give an unpleasant feeling to a driver and passengers. Particularly recently, when the use of air conditioners in cars is widespread and cars often run with the interior thereof tightly closed, quietness in the car interior is required and much attention is paid to the above-mentioned noises. Therefore, design and maintenance of a car are reviewed and pointed out from this point of view.

These kinds of problems were also pointed out in the past, and proposals were made in order to solve these problems.

For example, Japanese Utility Model Publication No. Sho 43-11746 discloses a vibrator as a noise locator comprising a motor, a main shaft rotatably connected to the motor, an eccentric portion having a bearing and disposed at a tip portion of the main shaft, and a shaft fixed to a swinging cover and engagable with the bearing, one end of the cover being pivotally attached, the other end of the cover being provided with a spindle which is able to accommodate an attachment therein, the attachment being situated in a predetermined position of an automotive vehicle, and the automotive vehicle being vertically vibrated in accordance with the activation of the motor.

However, as this conventional device includes a motor as a driving source, the device necessarily becomes large and heavy. Moreover, it takes much time and labor for rotating a crack handle when the amplitude of the vibration is changed. In addition, as a release in introduced into the car room when frequency of amplitude is regulated, noises enter the car room from outside through the opening for the release. The result is that any unusual noise in the car interior is masked by the outside noises, and is thus unable to be heard.

On the other hand, another type of vibrator is put into actual practice. This device is of a hydraulic type, instead of a mechanical type including a link mechanism and a cam mechanism as mentioned above, which directly vibrates tires through a hydraulic servo cylinder and indirectly vibrates the body of a car.

The hydraulic servo cylinder is actuated by a servo amplifier and a servo valve. The mode of operation of the hydraulic servo cylinder is in accordance with an optional frequency and wave form output by the servo amplifier. The structure of the hydraulic servo cylinder, as shown in FIG. 1, is such that a piston C provided with piston rods a and b projecting from both sides thereof is disposed within a cylinder housing d, pressure receiving areas thereof being horizontally equally formed. The same quantity of hydraulic oil is fed to pressure chambers e and f so that the piston rods a and b can reciprocally be moved at same speed in the horizontal direction.

Therefore, in such a cylinder as mentioned above, as both the piston rods a and b are projected outside the cylinder housing d, there is required a minimum length equal to a sum of the projecting lengths ($L_4+L_5$) and the strokes ($L_2+L_3$) of the respective cylinders. If the length of a support member for supporting the whole cylinder is added thereto, the total length becomes considerably long. Therefore, in device for directly vibrating the body of an automotive vehicle, such a large equipment is difficult to be disposed in a narrow space between a lower part of the vehicle body and a test base.

In a method for directly vibrating the tires through a hydraulic servo cylinder and indirectly vibrating the body of the automotive vehicle as mentioned above, as the vibration is applied through a suspension system, a large amplitude of vibration is required. As a result, a cylinder having a large output power is required. Therefore, the device becomes large and expensive, and is difficult to carry.

As a compact fluid pressure cylinder, there is known an air pressure cylinder, as disclosed for example in Japanese Utility Model Early Laid-open Publication No. Sho 56-106211, which comprises a cylinder body, a piston slidably disposed within the cylinder body, a piston rod integral with the piston, a shaft portion formed therein with a flow passage communicating with a pressure chamber and disposed within the piston rod, and an electromagnetic valve communicating with the flow passage so that pressurized air is fed and discharged therethrough.

However, this conventional cylinder is complicated in structure. Moreover, as a first head chamber, when operating, is pressurized through an accumulator and the piston rod is energized upward, an upper end of the rod is projected to that extent, which naturally jeopardizes any attempt to make compact the length of the cylinder.

SUMMARY OF THE INVENTION

One object of the present invention is to provide a vibrator which is capable of identifying an unusual noise generated from an object to be tested and accurately locating the place generating the noise.

Another object of the present invention is to provide a vibrator which is small light, and which is easy to carry in which amplitude and frequency of vibration can easily and rapidly be regulated, and which is inexpensive to manufacture.

A further object of the present invention is to provide a vibrator which includes a fluid pressure cylinder having shortest possible length in the axial direction so that it can be inserted into a narrow space between an object to be tested and a test base.

A still further object of the present invention is to provide a vibrator which is capable of identifying a squeaking noise of a vehicle body, a rattling noise of interior equipment, etc., accurately locating the place generating the noise, in which the unusual noises can be reproduced, which can be utilized in design, maintenance and inspection of an automotive vehicle, and which is suitably used as a vibrator of an automotive vehicle.

A yet further object of the present invention is to provide a vibrator, in which its length in the axial direction is made as short as possible and an upper end portion thereof is loaded with an object to be tested, such as an automotive vehicle, etc., and the vibration is amplified at a desired frequency and amplitude.

The vibrator of the present invention comprises a hydraulic circuit connected with a hydraulic power unit. An electromagnetic valve is disposed at the hydraulic circuit, the electromagnetic valve being regulated for the time for actuating a switch valve through a control signal. A plunger bears a load of an object to be tested at an upper end portion thereof, and has an oil chamber for pressurizing the plunger in such a manner as to be able to move upward and downward. An oil passage communicates with the oil chamber and with the electromagnetic valve. A vibration applying cylinder is capable of vibrating the plunger at a desired amplitude and frequency through hydraulic oil fed from the electromagnetic valve. A lift means lifts the vibration applying cylinder to a predetermined height. A controller is capable of outputting, as a control signal, a setting signal for setting at least the amplitude and frequency of the plunger. A control unit actuates the hydraulic power unit and the electromagnetic valve in accordance with the control signal.

From another aspect of the present invention, a vibrator comprises a hydraulic circuit connected with a hydraulic power unit, a base plate able to be disposed on a test base, and a ram to and from which hydraulic oil is fed and discharged through the hydraulic circuit. A pair of lift cylinders are each fixed at one end thereof to a movable plate which is movable with respect to the base plate, and each contain therein a cylinder tube which vertically movably accommodates therein a ram. A switch valve controls hydraulic oil so that the hydraulic oil is fed to and discharged from the cylinders. A pair of support members are each fixed to the movable plate. A vibration applying cylinder is pivotably supported between the pair of support members. An electromagnetic valve feeds and discharges hydraulic oil to and from the vibration applying cylinder. A control unit controls the action of the electromagnetic valve and the hydraulic power unit, and a plunger is vertically movably accommodated in the vibration applying cylinder which, when applying vibration, is able to bear the load of an object to be tested at an upper end portion thereof. A position sensor is disposed on a peripheral surface of the vibration applying cylinder and includes a guide tube which can be moved in unison with the plunger so as to detect the position of the plunger and input a detected signal into the control unit. A roller is rotatably axially supported by a pair of roller brackets fixed to the base plate, and an longated handle is fixed at one end thereof to the base plate.

From a further aspect of the present invention, a vibrator comprises a hydraulic circuit connected with a hydraulic power unit and a vibration applying cylinder including a plunger able to be attached with a spacer and an attachment. The plunger is moved upward and downward by means of hydraulic oil fed from and discharged to the hydraulic circuit and, when applying vibration, is able to bear a load of an object to be tested at an upper end portion thereof. A lift means is capable of lifting the vibration applying cylinder to a predetermined height, and an electromagnetic valve interposed between the vibration applying cylinder and the hydraulic circuit is adapted to feed hydraulic oil capable of activating the plunger at a desired amplitude and frequency with respect to the vibration applying cylinder.

The above and other objects and features of the present invention will become more apparent from the following detailed description taken in conjunction with the accompanying drawings.

BRIEF DESCRIPTION OF THE DRAWINGS

FIG. 4 is a front view showing one embodiment of the present invention;

FIG. 5 is a plan view of FIG. 4;

FIG. 6 is a right-hand side view, slightly enlarged and partly in section, of FIG. 4;

DETAILED DESCRIPTION OF THE PREFERRED EMBODIMENT

Figure 1:
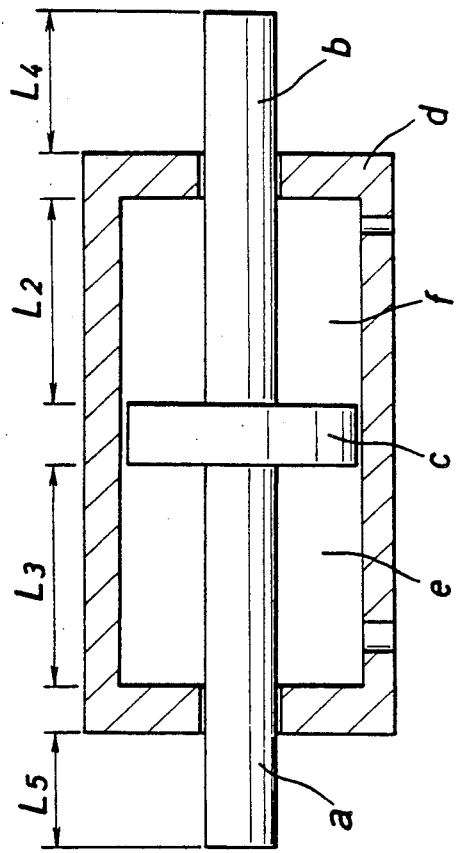
FIG. 1 is a sectional view showing one example of a conventional hydraulic servo cylinder.

The illustrated embodiment, in which the present invention is applied to a vibrator for the use of an automotive vehicle, will be described.

In FIG. 2 through FIG. 21, 1 denotes a vehicle to be tested as an object to be tested, which enters into a flat and stationary test space 2 of a maintenance factory or the like. A vibrator 4 is disposed at a lower portion of a side member, and a suspension gusset of a shaft body 3 of the front wheels acts as a portion receiving the vibration. The vibrator 4 is provided at its lower portion with a base plate 6, which is provided with shock absorbing plates 5 attached to a lower surface thereof (FIG. 3). Therefore, the vibrator 4 can be installed on the test base 2 through the plates 5. Disposed at both sides of the base plate 6 are a pair of lift cylinders 7 as means for lifting a vibration applying cylinder, as will be described afterward. Movable plates 8 can be moved through the cylinders 7.

Each of the movable plates 8 is formed with a passage hole 9 for permitting a cylinder tube to be inserted therein, as will be described afterward, and a slit-like cut-out portion 10 (FIG. 5) comprising a part of the hole 9 opening up at a rear end surface of the plate 8. The pair of lift cylinders 7 have generally the same construction with respect to each other. Each of the lift cylinders 7 includes a cylinder tube 11 having a closed upper end portion and a ram 12 as shown in FIG. 6.

Of these component parts, a lower end of the cylinder tube 11 is inserted into the passage hole 9 and held in the passage hole 9 by means of a bolt 13 bolted into two parts of the plate 8 laid at both sides of the cut-out portion 10. Furthermore, the cylinder tube 11 is more firmly secured to the plate 8 by means of a retaining ring 15 engaged in an annular groove 14 formed in the peripheral surface of a lower end portion of the tube 11. The cylinder tube 11 is formed at an upper end portion thereof with a through hole 16 which is connected with an oil coduit 17 communicating with a manual switch valve as will be described below.

On the other hand, a lower end portion of the ram 12 is inserted into a holder 18 which is secured to the base plate 6, and is fixed to the holder 18 by a machine screw applied from sideward of the holder 18. The ram 12 is provided at an upper end portion thereof with a seal plate 19 and defines an oil chamber 20 within the cylinder tube 11 through the plate 19. Secured to the inner sides of the movable plates 8 is a generally C-shaped guard frame 21 (see also FIG. 6) acting as a supporting member of a vibration applying cylinder, as will be described below. The frame 21 is provided at an inner side thereof with a vibration applying cylinder 23 swingably supported thereon through pins 22.

Figure 7:
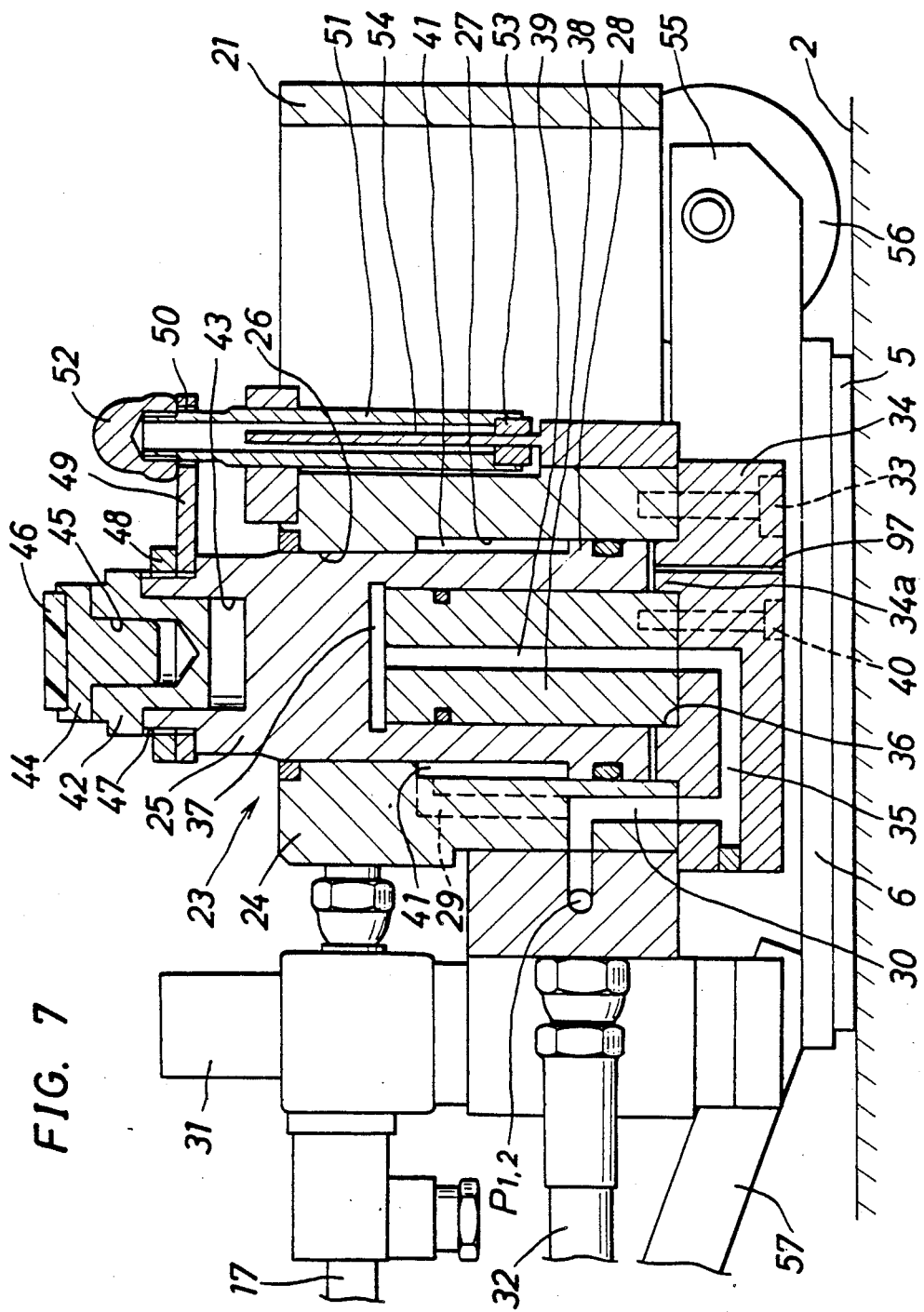
FIG. 7 is an enlarged sectional view taken on line VII—VII of FIG. 5.

The vibration applying cylinder 23 includes a cylindrical block 24, and a plunger 25 slidably mounted on the block 24. The cylinder block 24 is formed therein with sliding bores 26 and 27 having small and large diameters and communicated with each other as shown in FIG. 7. The plunger 25 is formed at a lower end portion thereof with a large diameter section 28. The plunger 25 is slidably accommodated within the sliding bores 26 and 27, and an upper end portion of the plunger 25 is projected upward from an upper end of the cylinder block 24.

Also, the cylinder block 24 is formed therein with an oil passage 29 opening up at the large diameter side of the sliding bore 27 and an oil passage 30 opening up at the lower end portion thereof. The other ends of the oil passages 29 and 30 are opened up at a rear end face of the cylinder block 24.

The cylinder block 24 is provided at the rear end face with an oil passage communicated with inlet/outlet port 5 P$_1$, P$_2$ of an electromagnetic valve 31 (FIGS. 5 and 8) which is capable of varying the amplitude and frequency of the plunger 25. The valve 31 is connected with an oil conduit 32 communicated with a hydraulic power unit as will be described, so that hydraulic oil can be fed to and discharged from the oil passages 29 and 30.

The cylinder block 24 (FIG. 7) is provided with a cover 34 secured to the lower end portion by means of a bolt 33. The cover 34 is formed therein with an oil passage 35 which is communicated with the oil passage 30. The cover 34 is formed at an upper end portion thereof with a convex portion 34a having a concave portion 36 formed at its center. The convex portion 34a is engaged with an opening portion at the lower side of the sliding bore 27. As a result, the cover 34 is abutted against the large diameter section 28.

The plunger 25 is provided therein with an oil chamber 37, and the oil chamber 37 accommodates therein a sleeve shaped plunger guide 38. The guide 38 has formed therein with an oil passage 39 communicating with the oil passages 35 and 37. A lower end of the guide 38 is accommodated in the recess 36 and secured to the cover 34 by means of a bolt 40.

In FIG. 7, 41 denotes an annular oil chamber defined by an inner peripheral surface of the sliding bore 27 and a peripheral surface of the plunger 25. The chamber 41 is communicated with the oil passage 29.

Figure 15:
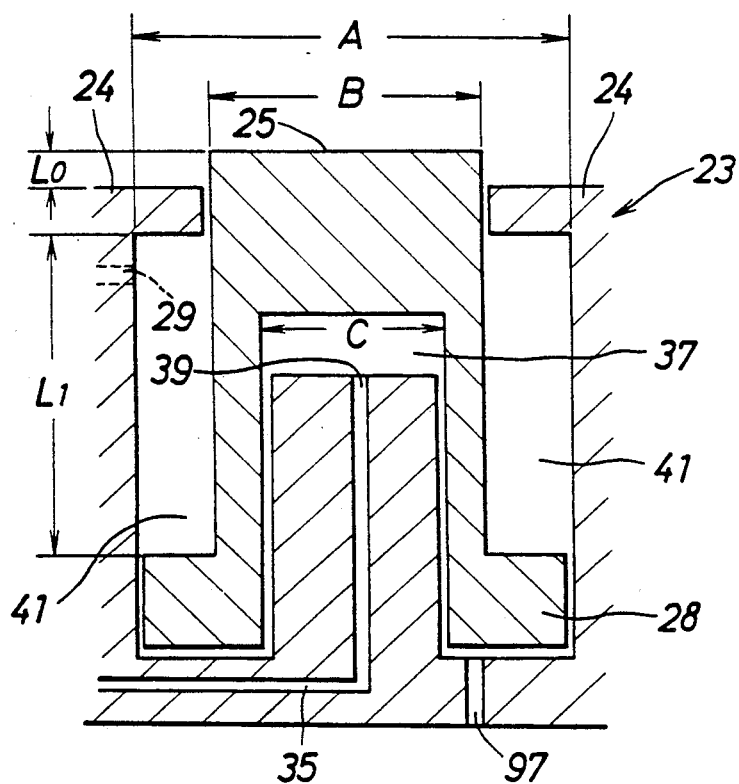
FIG. 15 is a sectional view showing a vibration applying cylinder which is applied to the present invention in such a manner as is convenient to explain its principle.

Characteristic structure of the vibration applying cylinder 23 is illustrated in FIG. 15 in such a manner as is convenient to explain its principle. The diameter of the oil chamber 41 is A, the outer diameter of the plunger 25 facing the chamber 41 is B, and the diameter of facing the chamber 41 is B, and the diameter of the oil chamber 37 is C. Among them, there is established a relation of $C^2 = A^2 - B^2$. A pressure receiving surface of the oil chamber 41 is identical with the pressure receiving surface of the oil chamber 37.

On the other hand, the plunger 25 (FIG. 7) is provided with a cavity 43, opening up at an upper end surface of the plunger 25, and adapted to removably accommodate a spacer. The spacer 42 is formed with a cavity 45 adapted to removably accommodate a boss 44a (see FIGS. 12-14) of an attachment 44. The attachment 44 has attached thereon a shock absorbing plate 46 which can be contacted with a portion to be applied with vibration.

The attachment 44 may be of various kinds, as shown in FIG. 12 through FIG. 16, so that they can be selectively used in such a manner as to cope with the state of a lower portion of a vehicle body, which is different for each kind or each model of a vehicle. The attachment 44 of FIG. 12 comprises a generally disk-shaped framework 44b and a shock absorbing plate 46 having a slightly smaller diameter and projecting therefrom. The attachment 44 of FIG. 13 comprises a framework 44b formed into a laterally elongated rectangular shape and an engaging projecting portion 44c projecting from one end or both ends thereof. The attachment 44 of FIG. 14 comprises a framework 44b formed into a rectangular shape and an engaging groove 44d formed in the center of an upper surface thereof.

Also, the plunger 25 (FIG. 7) is formed at a peripheral surface of an upper end portion thereof with a screw portion 47. The screw portion 47 is threadedly engaged with a ring nut 48 to thereby fix a sensor holder 49 mounted on its peripheral surface. A tip of the sensor holder 49 is expanded forward and a tip portion thereof is formed with a passage hole 50. The hole 50 is provided with a guide tube 51 inserted therein. The guide tube 51 is provided with a bag nut 52 so as to secure the tube 51 to the sensor holder 49.

The guide tube 51 is provided with a sensor sleeve 53 fixed to a lower end thereof. A long sensor core 54 containing therein a coil and constituting a position sensor, such as a differential transformer, etc., is inserted into the sleeve 53 such that the core 54 is not contacted with the sleeve 53. Variation of inductance owing to a positional change establishes a voltage, which is converted and input into a control unit as a position signal, as will be described.

In FIG. 7, 55 denotes a generally C-shaped roller bracket secured to each side of front end portions of the base plate 6, and a roller 56 is axially rotatably supported by the front end portion. Further, a rear end portion of the plate 6 is fixed with a base portion of a generally U-shaped handle 57. The handle 57 is provided with a leg 58 (see FIG. 4) projecting downward from an intermediate position in the longitudinal direction of the handle 57.

The handle 57 is fixed at an intermediate position with a valve box 60 through a bridge plate 59 (FIGS. 4–5). The box 60 is connected with the oil conduits 17 and single ends of threeway couplers 61, which are connected with the oil conduits 32. The box 60 is provided with a manual switch valve 62 mounted thereon.

Upon operation of a lever 63, the switch valve 62 permits a hydraulic oil to be fed to the lift cylinders 7. Numbers 64 denote oil conduits connected with the other ends of the three-way couplers 61, and are removably connected with a hydraulic power unit 66 through hose couplers (rapid disconnect couplers) 65 (see FIG. 8). Number 67 in FIG. 5 denotes a signal cable which is continued to the electromagnetic valve 31. The cable 67 is removably connected with the control unit 123 through a plug socket 68.

In FIG. 5, number 69 denote elongated tuning links which are secured at one ends thereof to both sides of the guard frame 21, and the other ends of the links 69 are fixed to a rod 70. The handles 57 disposed at both sides of the rod 70 are fixed with brackets 71. The handles 57 pivotally support the other ends of the links 69, 69 through pins 72 attached to the brackets 71.

Figure 2:
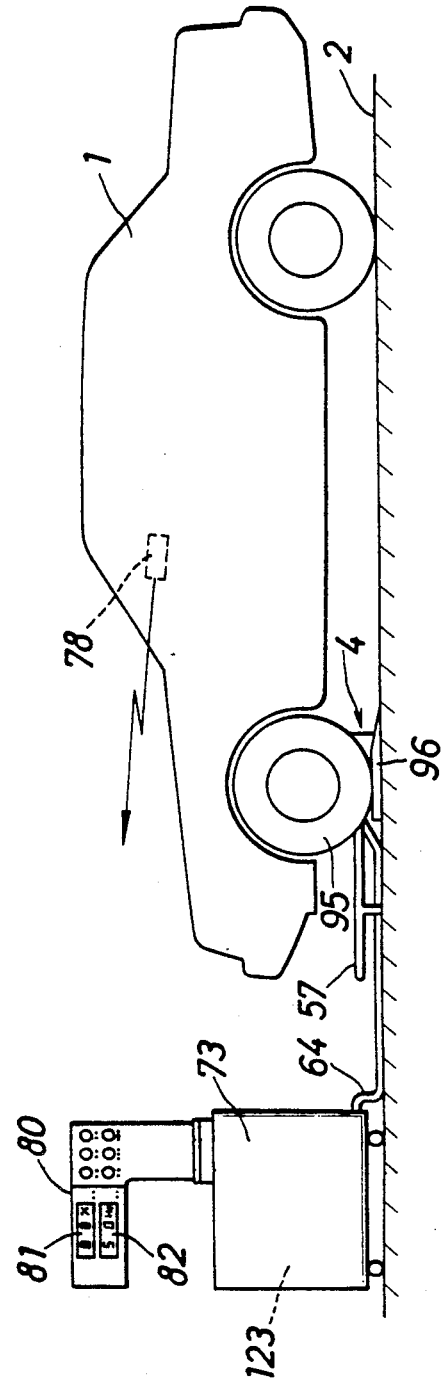
FIG. 2 is a schematic view showing a testing state where the present invention is applied to a vibration test.
Figure 3:
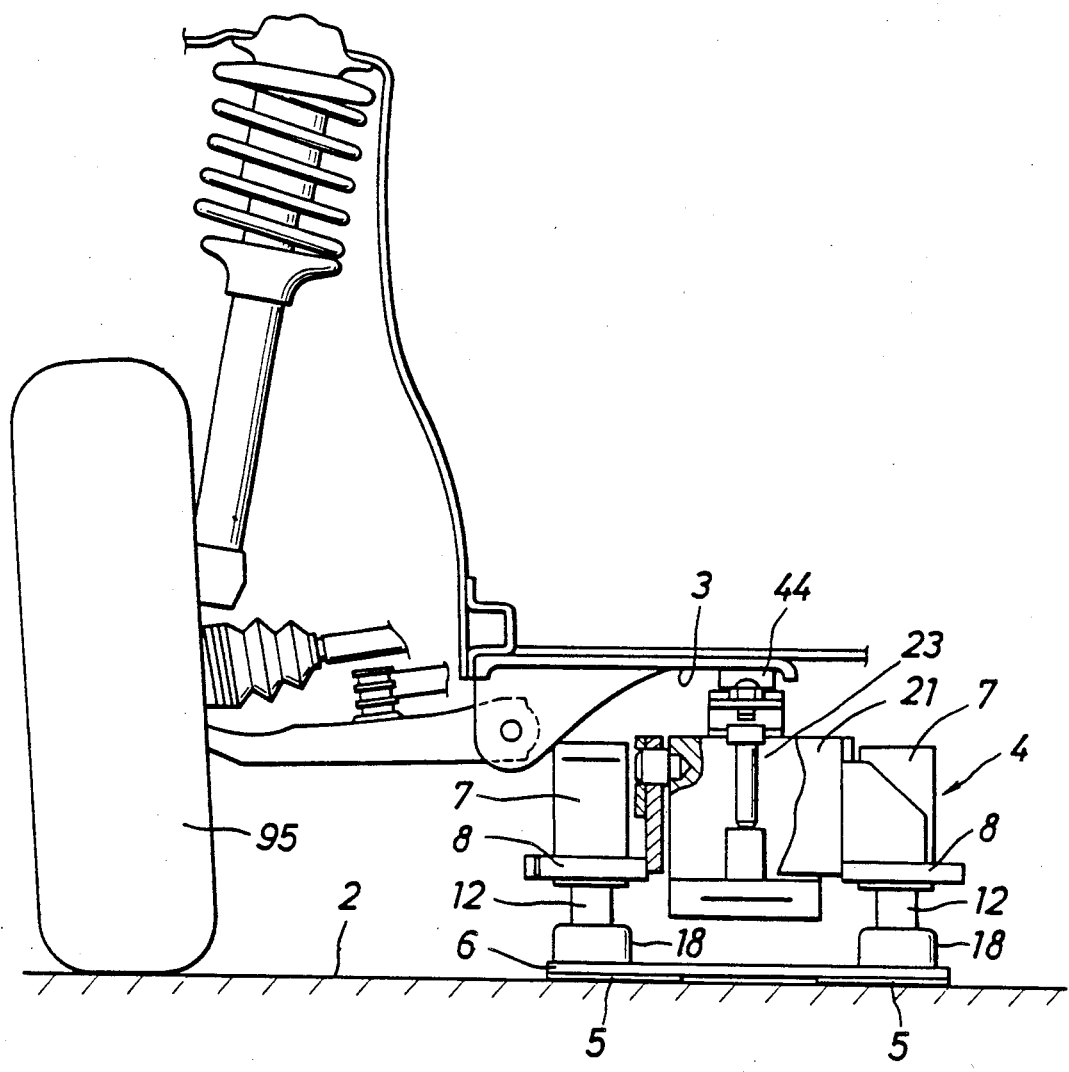
FIG. 3 is a front view, partly in section, showing an installation of a vibrator in its enlarged scale.
Figure 8:
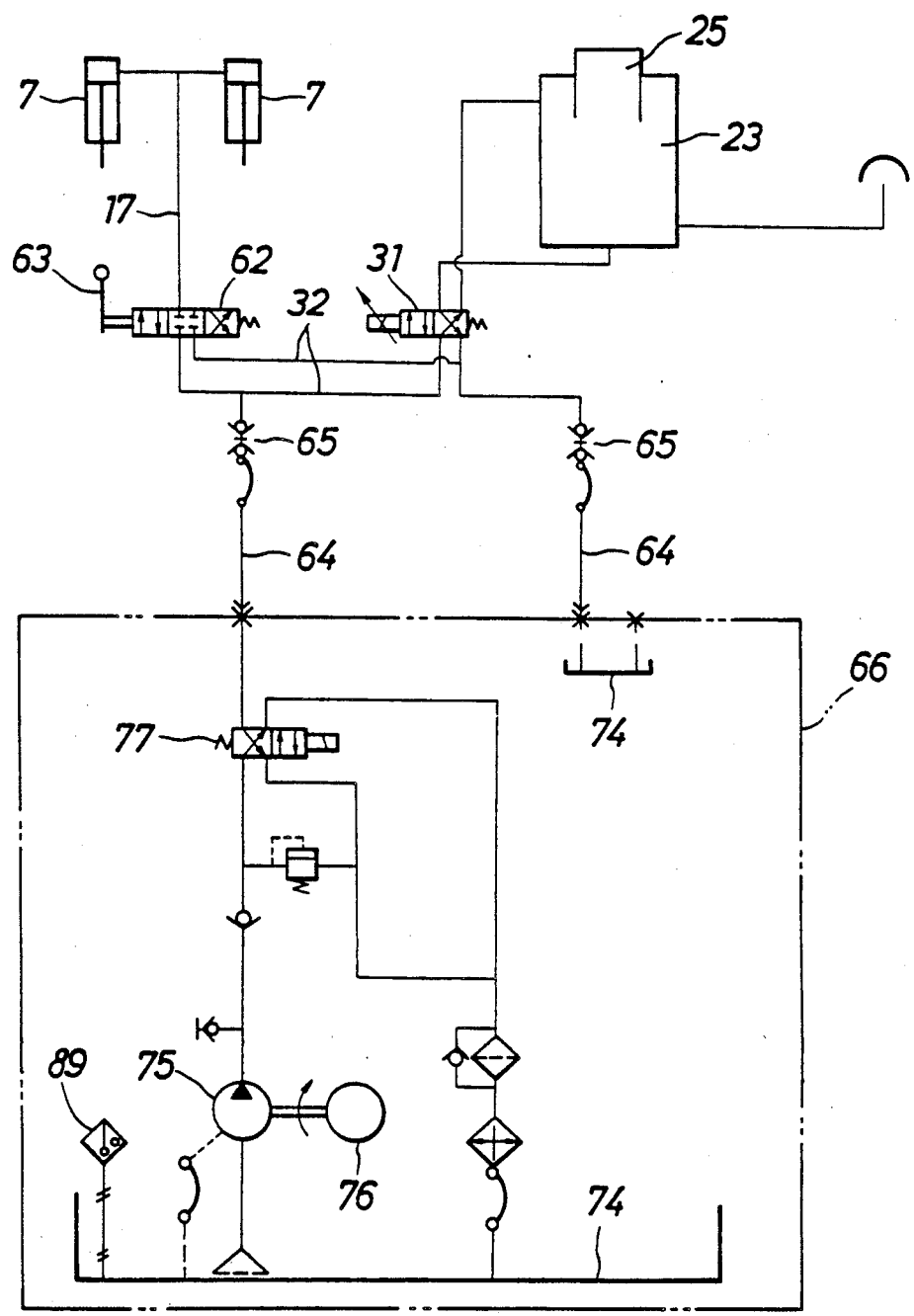
FIG. 8 is a hydraulic circuit diagram which is applied to the present invention.
Figure 11:
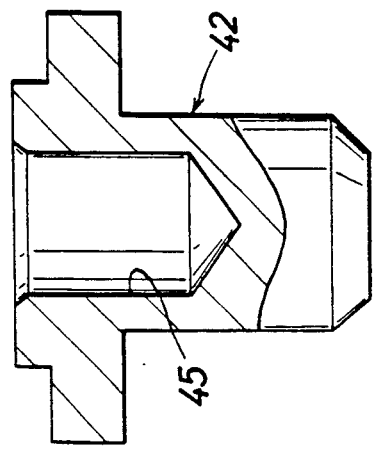
FIG. 11 is a partially sectional view showing one example of a spacer which is applied to the present invention.
Figure 10:
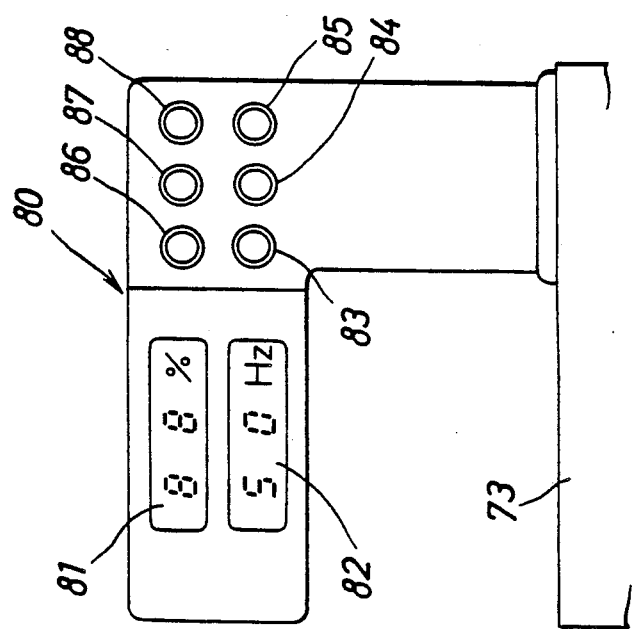
FIG. 10 is a front view showing a displayer which is applied to the present invention.
Figure 9:
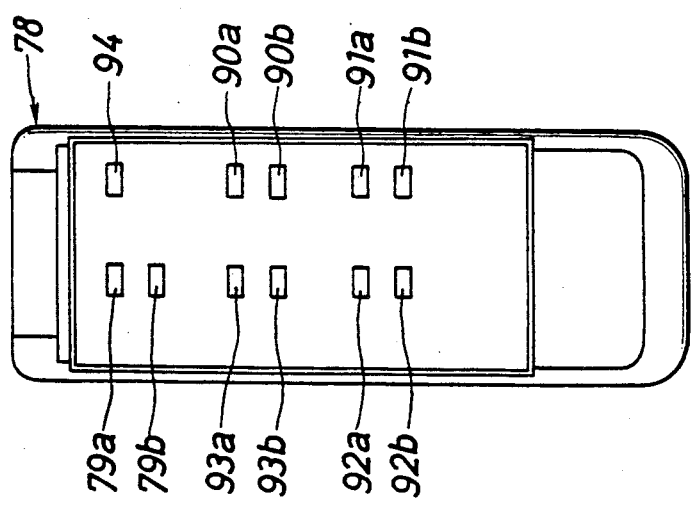
FIG. 9 is a front view showing one embodiment of a remote controller which is applied to the present invention.
Figure 12A:
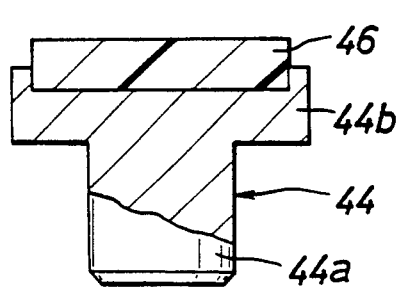
FIG. 12(a), FIG. 13(a) and FIG. 14(a) are front views, partly in section, showing various embodiments of attachments which are applied to the present invention.
Figure 12B:
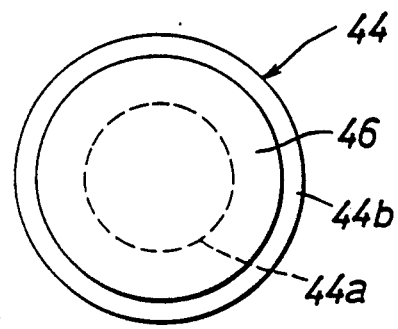
FIG. 12(b), FIG. 13(b) and FIG. 14(b) are plan views corresponding to FIG. 12(a), FIG. 13(a) and FIG. 14(a), respectively.
Figure 13A:
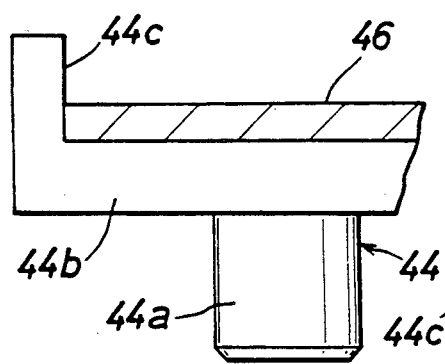
Figure 13B:
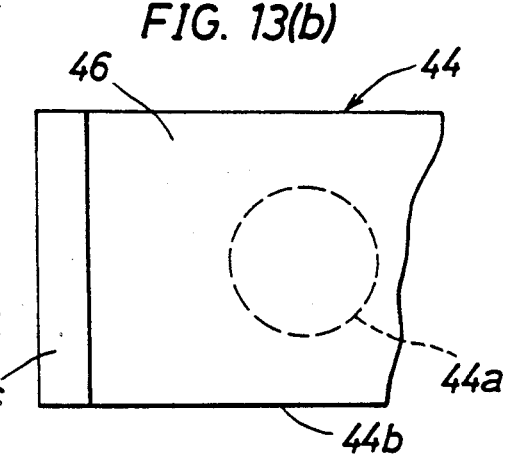
Figure 14A:
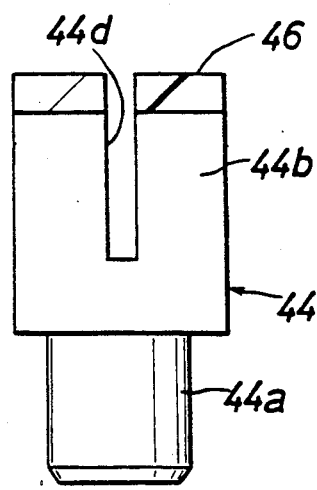
Figure 14B:
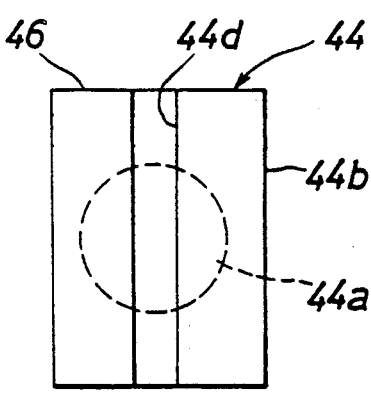

The hydraulic power unit 66 is accommodated in a control unit 73 (FIG. 2). The unit 66, as shown in FIG. 8, includes a variable flow rate type hydraulic pump 75 communicated with a hydraulic tank 74, a drive motor 76 for actuating the pump 75, and an unload valve 77. The pump 75 and the motor 76 can be switched on and off according to on/off operation of a pump switch disposed at a display, as will be described below. Also, the unload valve 77 is brought to onload position or unload position by means of on/off operation of hydraulic switches 79a and 79b, (FIG. 9) as will be described below. In the figure, 79a denotes an on-switch and 79b denotes an off-switch.

The control box 73 is provided with the control unit 123 (FIG. 2) containing therein a control circuit. This circuit comprises a signal receiving circuit including, for example, a light receiving element capable of receiving an input signal from a remote controller 78 and a decoder for interpreting the received signal, a logic circuit for outputting a control signal, under a predetermined condition, in accordance with a signal from the signal receiving circuit, and an output control circuit for outputting a predetermined signal to a display 80.

The display 80 (see FIG. 10) is integrally mounted on an upper portion of the control box 73. The display 80 is provided, at an upper position of its front surface, with an amplitude displaying portion 81 for digitally displaying the ratio between the maximum amplitude and the established amplitude at the established frequency in percentage, and a frequency displaying portion 82 for digitally displaying the established frequency. The displayer 80 is also provided at the side of the amplitude displaying portion 81 and the frequency displaying portion 82 with a plurality of indicating lamps 83 and 86 through 88, and switches 84 and 85 for actuating and stopping the pump and also serving as indicating lamps.

More specifically, 83 is an electric power indicating lamp for indicating the "on" position of the electric power, 84 and 85 are pump actuating and stopping position indicating lamps for indicating the "on-off" position of the hydraulic pump 75, 86 is an oil pressure indicating lamp for indicating an onload position of the hydraulic circuit, 87 is a vibration applying cylinder position indicating lamp which lights up when the vibration applying cylinder is in the lowest position, and 88 is an oil temperature indicating lamp which is lighted up when a predetermined oil temperature is detected through a thermostat (FIG. 8).

On the other hand, the remote controller 78 (FIG. 9) contains therein a transmitting means such as a light emitting diode, etc., which is capable of transmitting a signal to the signal receiving circuit. The remote controller 78 is provided on an outer surface thereof with cylinder position switches 90a and 90b capable of establishing the vibration applying cylinder 23 at an intermediate position ($\frac{1}{2}$ of the whole stroke) and a lowest (lower end) position, frequency and amplitude switches 91a and 91b, and 92a and 92b, capable of variably establishing frequency and amplitude (in the embodiment, capable of establishing frequency and amplitude at the up or down position), manual switches 93a and 93b capable of moving the vibration applying cylinder 23 upward and downward at a frequency of about 0.2 HZ (93a is an upward switch and 93b is a downward switch), and an emergency stop switch 94 for abruptly stopping all actions in an emergency.

In this case, there can be provided the display portions 81 and 82 mounted on the displayer 80 and also the various indicating lamps 83 through 88 on the remote controller 78. Owing to the foregoing arrangement, the above-mentioned sequence of procedure can be carried out easily and effectively without watching the display 80 each time.

In FIG. 7, 95 denotes a front wheel of the vehicle 1 to be tested, 96 denotes a step, and 97 denotes an air channel (FIG. 7).

When a vibrator having the above-mentioned constitution is not in use, the oil conduits 64 are removed from the hose couplers 65 the signal cable 67 is removed from the plug socket, and these component parts are accommodated in the control box 73. Accordingly, as the box 73 and the vibrator 4 can be separated, accommodation and handling thereof become easy.

And, if the vibrator 4, when not in use, is erected with the front end face of the guard frame 21 fixed to the test base 2, the accommodating space can be reduced and the test base 2 can be used effectively.

Next, in a case wherein the object 1 to be tested is actually vibrated by using the vibrator 4, the object 1 is situated on the test base 2. At that time, a pair of steps 96 are arranged on the base 2, and either front or rear wheels of the object 1 are moved over the steps 96 in order to slightly heighten the ground clearance in order to secure a wide insertion space for the vibration applying cylinder 23.

Also, either slightly before or after the above, the oil conduits 64 and the signal cable 67 accommodated in the control box 73 are withdrawn and connected to the hose couplers 65 of the vibrator 4 and the plug socket 68, respectively, and are now in a position ready for use. On the other hand, an attachment 44 suitable for the front axle member 3 is selected. Then, such selected attachment 44 is inserted into the cavity 45 of the spacer 42 and the spacer 42 is inserted into the cavity 43 of the plunger 25. In this case, the plunger 25 of the vibration applying cylinder 23 is situated in the lowest position.

When such the above preliminary work has been finished, the electric power of the control box 73 is charged and the pump actuating switch 84 is turned on in order to actuate the hydraulic motor 6 and the hydraulic pump 75. This state can be confirmed by means of the lighting of the electric power indicating lamp 83 and the pump actuating switch 84. Similarly, the lowest position state of the vibration applying cylinder 23 can be confirmed by means of the lighting of the vibration applying cylinder position indicating lamp 87.

In this case, the amplitude indicating portions 81 and 82 cancel the previous indication and show a value of zero and 1 HZ. Also, when the hydraulic switch 79 of the remote controller 78 is in the off position, the hydraulic pump 75 is in the unload position.

Under the above-mentioned circumstances, a rear end portion of the handle 57 is held, and while slightly lifting the rear end portion of the handle 57, the truck is moved toward the front axle member 3. When the vibration applying cylinder 23 is brought to a position immediately under the front axle member 3, the truck is stopped.

In this case, the length of the vibration applying cylinder 23 in the axial direction, as shown in FIG. 15, is generally set to a sum of the full stroke $L_1$ and the projecting dimension $L_0$ from the cylinder block 24 of the plunger 25. When this is compared with the conventional cylinder of FIG. 1, the length of the conventional cylinder in the axial direction requires at least a total length of $L_2+L_3+L_4+L_5$ plus the length of the support members of the whole cylinder. Therefore, it will be understood that the length of the vibration applying cylinder can considerably be reduced.

Accordingly, the vibration applying cylinder 23 can be located in a very narrow space formed between the front axle member 3 and the test base 2. In addition, in order to facilitate the location of the vibration applying cylinder 23 in the narrow space, the guide tube 51 provided with the sensor sleeve 53 is disposed at the side of vibration applying cylinder 23 so as to limit the length of the cylinder 23. The spacer 42 is formed at the upper surface of the plunger 25 with the cavity 45 for accommodating therein the boss 44a of the attachment 44 so as to limit the height of the attachment 44 from the test base 2.

Moreover, as the vibration applying cylinder 23 is not an expensive hydraulic servo cylinder as in the prior art, it can be manufactured at low cost. In addition, as the lift to a predetermined height of the vibration applying cylinder 23 is borne by the lift cylinders 7, the vibration applying cylinder 23 can be made small in capacity, and the small size and light weight of the vibration applying cylinder 23 is enhanced.

Then the remote controller 78 is held and the hydraulic switch 79a is turned on to switch to an onload position. Thereafter, the lever 63 of the switch valve 62 is operated in the direction as indicated by an arrow of FIG. 5 in order to switch the valve 62 into an offset position so that hydraulic oil of oil conduit 64 is guided into the oil conduits 17 and fed into the oil chambers 20 of the lift cylinders 7 from the through hole 15 under pressure. The onload state is confirmed through the lighting of the hydraulic indicating lamp 86.

In this way, the pressure of the oil chambers 20 is raised and the cylinder tube 11 is moved upward. As a result, the movable plates 8 integral with the tube 11 and the brackets 21 are moved upward altogether. As a result, the vibration applying cylinder 23 pivotally attached between the brackets 21 is pushed up.

In this way, when the cylinders 7 are lifted, the attachment 44 attached to the upper ends thereof is brought into abutment against a lower portion of the front axle member 3. After a slight lifting thereafter, the lifting action is stopped. And, when the lever 63 is released after the lifting operation, the switch valve 62 is returned to a normal position and the lifted state is maintained by a blocking action.

In this case, in accordance with the upward movement of the lift cylinders 7, one end of the tuning links 69 fixed to the guard frame 21 are moved together, and the lift displacement is synchronized by the rod 70 fixed to the other ends. Accordingly, the vibration applying cylinder 23 is stably moved upward. Also, as the vibration applying cylinder 23 is pivotably supported by the pins 22 as mentioned above, even when a deflecting, or eccentric load acts on the attachment 44 or plunger 25 due to the abutment with the front axle member 3, the cylinder 23 pivots to cancel it and a certain degree of freedom is given to the abutting state of the attachment 44, and a reasonable vibrating state is formed.

Then, when the remote control 78 is held and the intermediate switch 90a of the cylinder position switch is turned on, a signal is output to the electromagnetic valve 31 from the control circuit. Then hydraulic oil is fed to the valve 31 and the plunger 25 is lifted upward to the level of $\frac{1}{2}$ of the whole stroke. As a result, the front axle member 3 is further pushed up. In this case, the lower end indicating lamp 87 is extinguished by means of the input of the signal.

In this way, when the front axle member 3, as an object to be applied with vibration, has been lifted to a predetermined height through the lift cylinders 7 and the vibration applying cylinder 23, a sequence of preparatory work is finished. Thereafter, a service man holds the remote controller 78 and gets in the vehicle 1 to be tested. Then he carries out the vibrating operation in the passenger compartment of the vehicle.

In this case, as the remote controller 78 is of a wireless type, the window glass is not required to be formed with an opening therein in order to draw a signal cable into the compartment of the vehicle as in a conventional type. Therefore the compartment of the vehicle can be maintained sealed.

The vibration applying operation is performed by increasing or reducing (up or down) the frequency of the remote controller 78 and the amplitude switches 91a and 91b and 92a and 92b, and establishing a desired frequency and amplitude with respect to the vibration applying cylinder 23. Such, signal is input into the control circuit from the remote control 78 and digitally indicated on the amplitude and frequency indicating portions 81 and 82. Therefore, the service man can easily establish the amplitude and frequency while watching the indicating portions 81 and 82.

In this way, when the established signal of the amplitude and frequency of the vibration applying cylinder 23 is input into the control circuit, an electric current signal, as a frequency signal, is output to the solenoid of the electromagnetic valve 31. Then the solenoid alternately actuates a spool in accordance with the electromagnetic force in order to switch the valve into a high speed position, so that hydraulic oil can be fed to and discharged from the cylinder 23 at a high speed.

That is, the hydraulic oil, which is fed from the port $P_1$ of the electromagnetic valve 31, is introduced into the oil chamber 37 via the oil passages 30, 35 and 39 under pressure. As a result, the pressure of the oil chamber 37 is raised to push up the plunger 25. At the same time, the hydraulic oil in the oil chamber 41 is discharged into the oil tank 74 from the port $P_2$. On the other hand, slightly before or after the time when the hydraulic oil is fed from the port $P_1$, the hydraulic oil, which is fed from the other port $P_2$ of the electromagnetic valve 31 under pressure, is introduced into the oil chamber 41 via the oil passage 29. As a result, the pressure in the oil chamber 41 is raised to push down the plunger 25. At the same time, the hydraulic oil in the oil chamber 37 is discharged into the oil tank 74 from the port $P_1$.

Also, when the amplitude signal is input into the control circuit, a voltage signal, as an amplitude signal, is output to the solenoid of the electromagnetic valve 31. As a result, the spool is alternately changed in stroke by the solenoid in accordance with the electromagnetic force, and an opening amount with respect to the ports $P_1$ and $P_2$ *is increased and decreased alternately. As a result, the amount of oil to be fed to the oil chambers 37 and 41 of the vibration applying cylinder 23 is increased and decreased alternately. As a result, the stroke of the plunger 25 is changed to control the amplitude.*

The displacement of the plunger 25 in this case is detected by the sensor core 54 provided with a sensor sleeve 53 which acts in unison with the plunger 25, and the signal is input into the control circuit so as to be fed back to the amplitude control. As a result, amplitude of the plunger 25 is stabilized.

In this way, when the vibration applying operation is effected, the front axle member 3 is vibrated at the same amplitude and frequency as the vibrator 4. As result, a squeaking noises of the vehicle body and a rattling noises of the interior equipment of the vehicle can be generated.

As the vibration applying operation is carried out in a sealed compartment of a vehicle as described above, the unusual noise can be identified and the place for generating the unusual noise can be located correctly. This is one of the significant features of the present invention when compared with the prior art, where outside noises invades into the compartment of the vehicle through an opening formed in the window glass, which naturally makes it difficult to distinguish a genuine unusual noise, from the outside noises and also difficult to hear or recognize a faint and weak noise. Thus, a high reliability for this kind of test can be obtained.

Furthermore, as the amplitude and the number of vibrations with respect to the vibration applying cylinder 23 are digitally indicated, and the indication is minute and precise, a particular amplitude and a particular number of vibrations can be established with ease, and reproduction of the unusual noise can be obtained.

After the vibration applying test is over, the amplitude switch 92b is operated to reduce the amplitude until it is set to a value of zero and the amplitude operation of the plunger 25 is stopped. At the same time, the electromagnetic valve 31 is activated to bring the vibration applying cylinder 23 to the lowest position. Further, the lever 63 of the switch valve 62 is operated in the direction opposite the direction as indicated by the arrow of FIG. 5 in order to return the hydraulic oil of the lift cylinders 7 to the oil tank 74 so as to lower the cylinders.

Then the hydraulic switch 79b is operated to establish the unload state, and thereafter, the pump stop switch 85 is operated to stop the hydraulic pump 75 and the motor 76. The oil conduits 64 and the signal cable 67 are removed and accommodated in the control box 73. Then the vibrator 4 is moved to a predetermined position and stored in its upright posture.

FIG. 16 through FIG. 21 show another embodiment of the present invention, wherein corresponding component parts to those of the preceding embodiment are represented by identical reference numerals.

Of these figures, FIG. 16 through FIG. 20 illustrate a vibrator 4 including lift cylinders 7 and a vibration applying cylinder 23 which are slightly different in construction from the corresponding parts of the preceding embodiment and a method for controlling the amplitude and frequency of the cylinder 23.

That is, a spring 98 (FIG. 17) for enhancing the contracting action of the ram 12 is disposed between an upper end portion of the cylinder tube 11 of the lift cylinder 7 and a lower end portion of the ram 12. The movable plate 8 disposed at an inner side of the tube 11 is provided with brackets 99 erected thereon. The brackets 99, 99 are provided with pins 22 projecting sideward of the vibration applying cylinder 23 and rotatably inserted into upper portions of the brackets 99.

The vibration applying cylinder 23 is provided with a first pair of oil passages 29a and (FIG. 18) and a second pair of oil passages 30a and 30b, which communicate with oil chambers 37 and 41 and open up at the peripheral surface of the vibration applying cylinder 23. End faces where at the oil passages open up are provided with a pair of high speed switch electromagnetic valves 100a and 100b, and 101a and 101b, respectively. These electromagnetic valves 100a, 100b and 101a, 101b have a considerably high responsibility such as, for example, a few millimeters per second, and can be switched to a high speed. These valves can also be selectively communicated with or discommunicated from an oil tank 74 or a hydraulic oil source 102 (see FIGS. 19-20).

The electromagnetic valves 100a and 101a are communicated with the hydraulic oil source 102, whereas the electromagnetic valves 100b and 101b are communicated with the oil tank 74. Furthermore, the electromagnetic valves 100a and 100b can be operated as one pair with the electromagnetic valves 101a and 100b.

For example, when one pair of electromagnetic valves 100a and 101b are turned on in order to be communicated with the hydraulic oil source 102 and the oil tank 74, the other pair of electromagnetic valves 100b and 101a are in an off-position in order to be discommunicated from the oil tank 74 and the hydraulic oil source 102. In other words, when one oil chamber 41 is in a communicating relation with the hydraulic oil source 102, the other oil chamber 37 is in a communicating relation with the oil tank 74.

Figure 19:
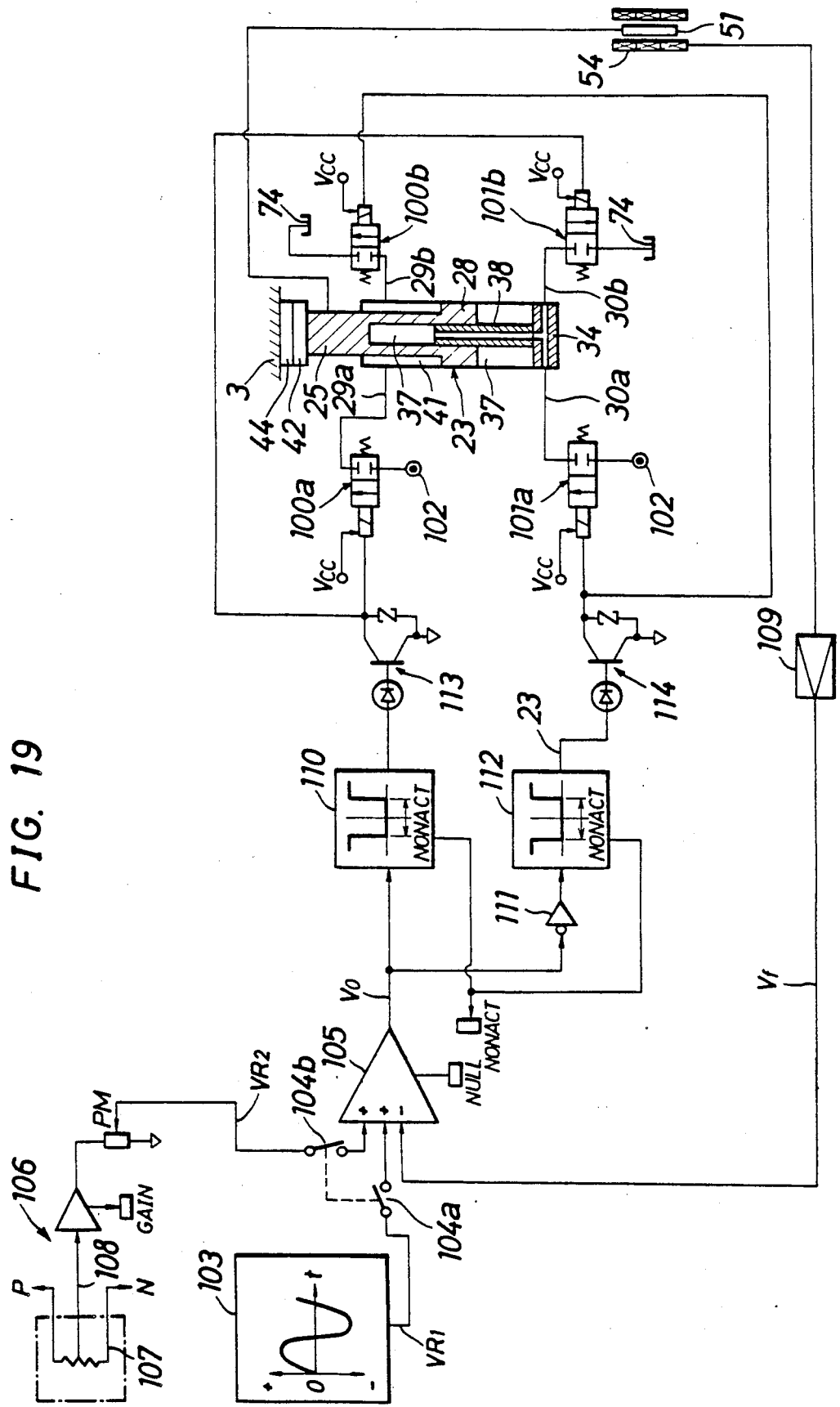
FIG. 19 is an electric circuit diagram showing one example of a method for controlling a vibration applying cylinder.

These electromagnetic valves 100a, 100b, 101a and 101b are controlled by an electric circuit as shown in FIG. 19. This electric circuit is connected with a function generator 103 for outputting a first command signal $VR_1$ of an optional frequency and an adder 105 input with the signal $VR_1$ through a switch 104a.

An input end of the adder 105 is connected with a joy stick device 106 for outputting a second command signal $VR_2$ through a switch 104b. The device 106 includes a joy stick lever 108 which is connected with high and low pressure electric power sources P and N through a variable resistor 107, so that the signal $VR_2$ having a pressure corresponding to inclination of the lever 108 can be output at a frequency corresponding to the number of times for switching the lever 108.

The first and second command signals $VR_1$ and $VR_2$ can selectively be input into the adder 105 through the switches 104a and 104b. Also, the adder 105 is fed back with a position detecting signal as a feed back signal $V_f$ from a sensor core 54. The signal $V_f$ is amplified to 0 through +10 V by an amplifier 109.

The adder 105 compares the first or the second command signal $VR_1$ or $VR_2$ with the feed back signal $V_f$ and outputs a control signal $V_o$ for moving the large diameter portion 28 of the plunger 25 in the direction where the signals $V_1$ or $V_2$ and $V_f$ are coincident with each other. The control signal $V_o$ is input into a first comparator 110 for establishing a first dead zone, and is simultaneously branched off and inverted into an opposite phase by an inverter 111 and input into a second comparator 112 for establishing a second dead zone.

In FIG. 19, 113 and 114 denote transistor switch devices interposed between the comparators 110 and 112 and the electromagnetic valves 100a, 101a and respectively. The devices 113 and 114 are activated such that when one pair of electromagnetic valves 100a and 101b are on, the other pair of electromagnetic valves 101a and 100b are off, and when the former is off, the latter is on. When the pair of electromagnetic valves 100a and 101b are on or off, the other electromagnetic valves 101a and 100b are not interfered with each other through the dead zones of the comparators 110 and 112.

In this vibrator, if the switch 104b is turned on to actuate the joy stick device 106, the signal $VR_1$ of the function generator 103 is unable to be put into the adder 105. And, as described previously, the second command signal $VR_2$ moves the plunger 25 upward and downward at a frequency corresponding to the number of times of switching operation of the joy stick lever 108 and at a plunger stroke, i.e., amplitude, corresponding to the angle of inclination of the lever 108.

Then, when the switch 104b is turned off and the switch 104a is turned on to input the first command signal $VR_1$ of the function generator 103 into the adder 105, there can be obtained an action of the plunger 25 corresponding to the frequency, wave form and amplitude which are output by the function generator 103.

Figure 20:
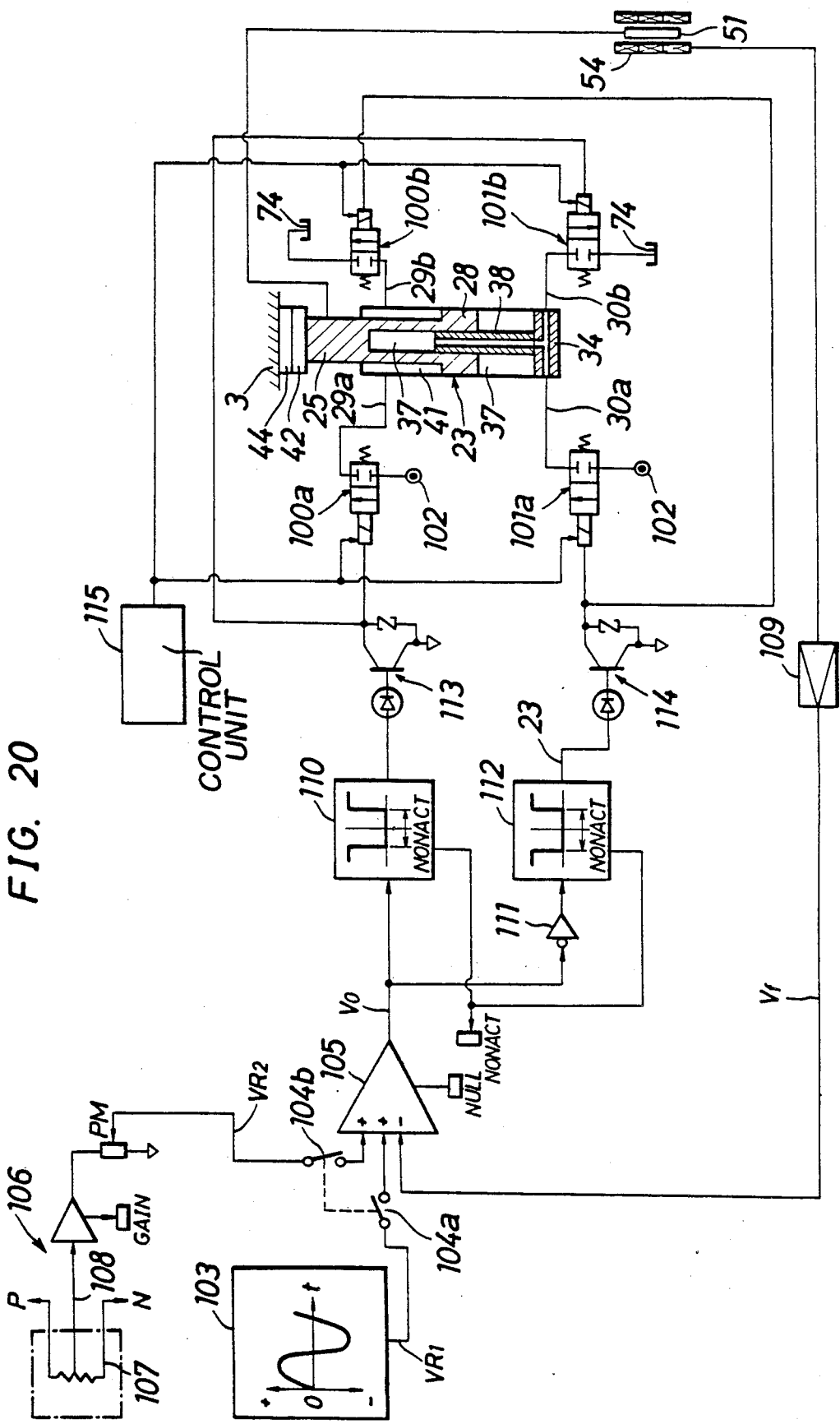
FIG. 20 is an electric circuit diagram showing another method for controlling a vibration applying cylinder.

FIG. 20 is a schematic block diagram showing another embodiment of the electric circuit and the hydraulic circuit, wherein identical component parts as those of FIG. 19 are represented by identical reference numerals, and description thereof will be omitted.

The vibrator in this embodiment includes a variable voltage control unit 115 for varying an incurring voltage of an exciting coil of the respective high speed switching electromagnetic valves 100a, 100b, 101a and 101b.

The variable voltage control unit 115 varies the incurring voltage of the exciting coil of the respective electromagnetic valves 100a, 100b, 101a and 101b. This eventually makes it possible to vary the opening and closing force of the valve (not shown in the figure) of the respective electromagnetic valves by the respective coils.

That is, when an incurring voltage, which has been controlled to a high pressure, is fed to the exciting coil, the electromagnetic valve is rapidly opened or totally opened. On the other hand, when an incurring voltage, which has been controlled to a low pressure, is fed to the exciting coil, the electromagnetic valve is slowly opened or half-opened.

With the constitution as mentioned, when the joy stick device 106 is used, the plunger 25 is moved upward and downward at a frequency corresponding to the number of switching times of the joy stick lever 108 and at a plunger stroke corresponding to the angle of inclination of the lever. When the incurring voltage is high, a large amount of hydraulic oil of the hydraulic oil sources 102 is flowed in and moved at a high rising speed, and the hydraulic oil in the pressure chambers 37 and 41 is also returned into the oil tanks 74 at a high rising speed. As a result, the moving speed of the plunger 25 is controlled to a high speed. On the other hand, when the incurring voltage is low, the plunger 25 is moved at a low rising speed and the moving speed is controlled to a low speed.

If the function generator 103 is used, the plunger 25 is also moved in such a manner as to correspond to the frequency, wave form and amplitude output by the function generator 103. However, the speed is variably controlled by the variable voltage control unit 115.

Figure 21:
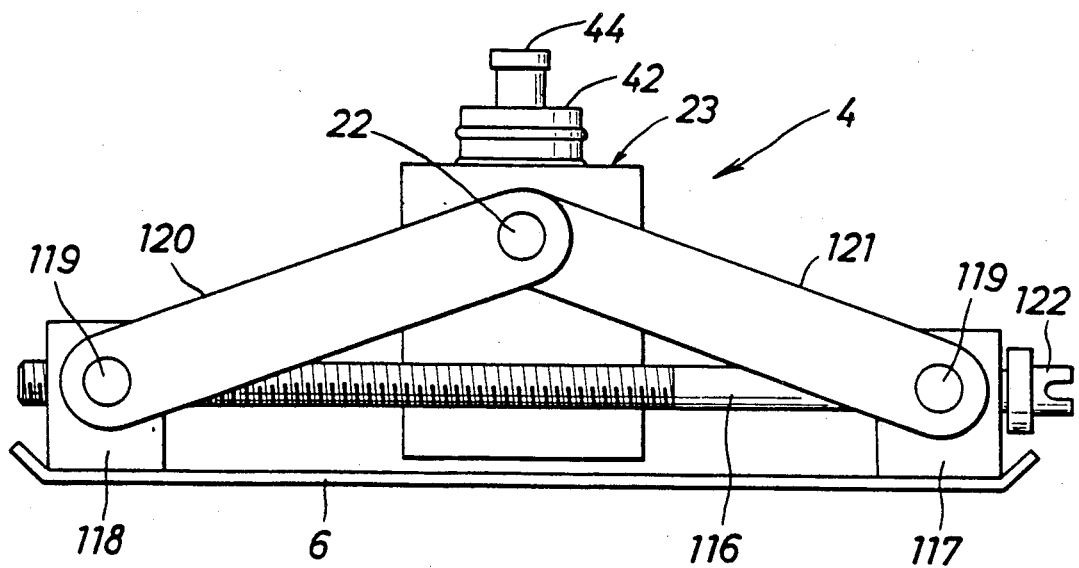
FIG. 21 is a front view showing a further embodiment of the present invention.
Figure 16:
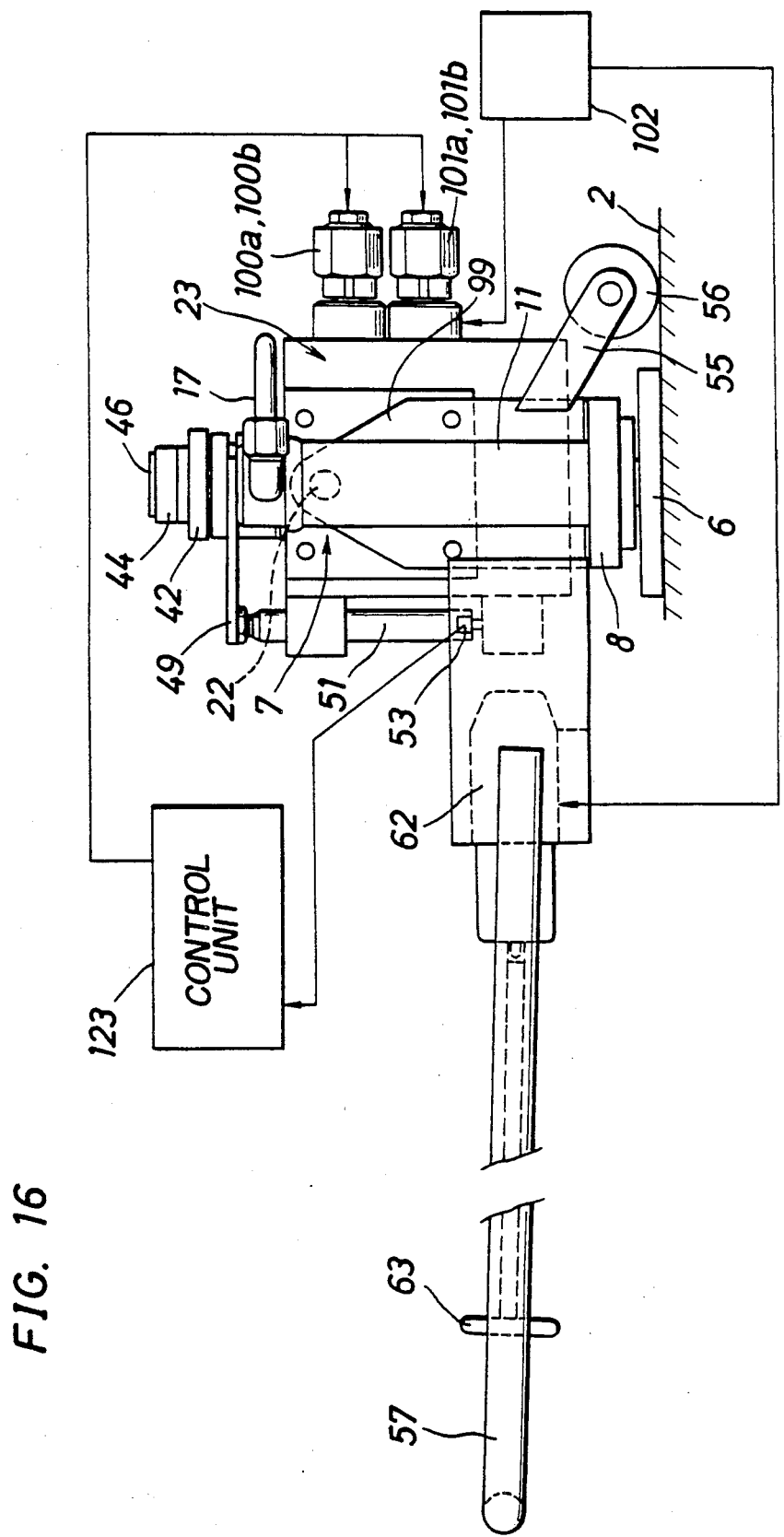
FIG. 16 is a front view showing another embodiment of the present invention.
Figure 17:
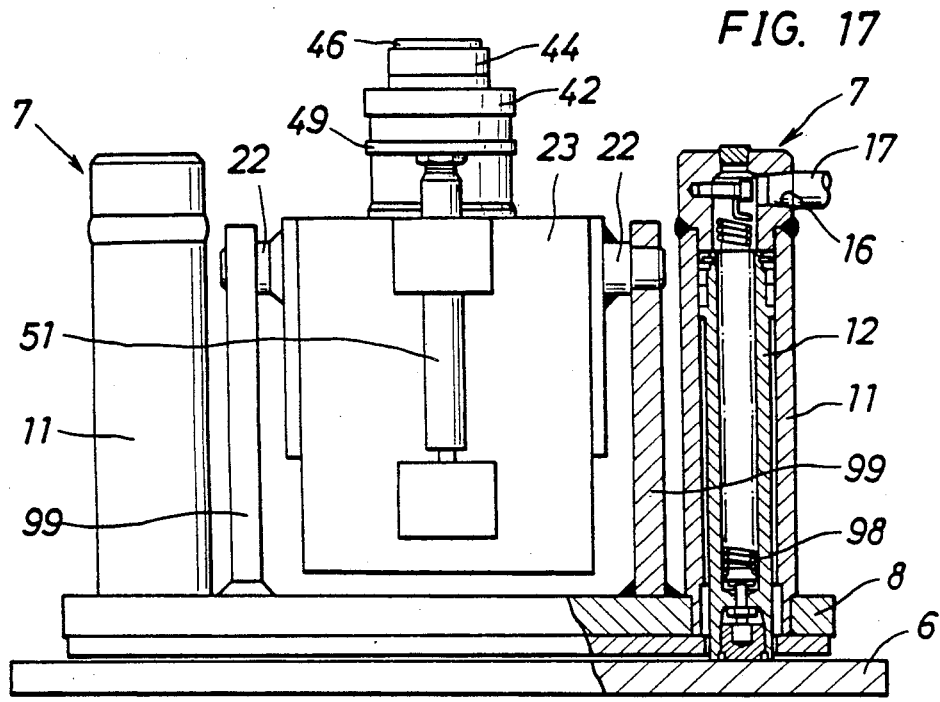
FIG. 17 is a partially sectional view showing an important portion of the embodiment of FIG. 16.
Figure 18:
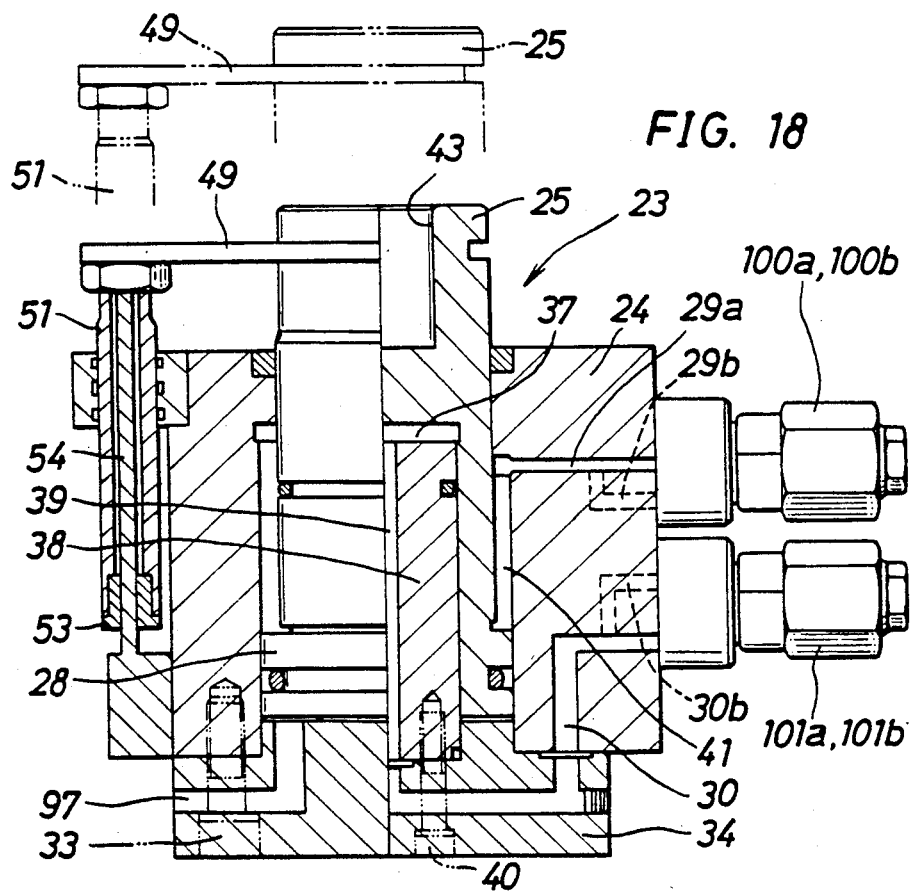
FIG. 18 is a sectional view showing another important portion of the embodiment of FIG. 16.

A vibrator 4 of still another embodiment of FIG. 21 uses a so-called pantograph type jack instead of the lift cylinder 7. A jack block 117 for pivotably supporting a screw shaft 116 is fixed to one end of a base plate 6, the other end thereof being movably provided with a movable block 118 which is engagable with the shaft 116. The block 118 is able to approach and move away from the block 117, the blocks 117 and 118 being pivotably connected at both sides thereof with links 120 and 121 through pins 119. The other ends of the links 120 and 121 are pivotably connected with a side of a vibration applying cylinder 23 through a pin 22.

If the vibration applying cylinder 23 is lifted to a predetermined height, a handle (not shown) is engaged with a dog 122 disposed at one end of the screw shaft 116 and the handle is simply rotated.

Therefore, this vibrator has the advantage that, since a mechanical type jack is utilized, the vibrator can be manufactured with ease and at low cost.

Although various embodiments of the present invention have been described above, it will be understood that the above description of the present invention is susceptible to various modifications, changes and adaptations which are intended to be comprehended within the meaning and range of equivalents of the appended claims.

What is claimed is:
1. A vibrator, comprising:
   an plunger for bearing an object to be vibrated at an upper portion of said plunger;
   a vibration applying cylinder for vibrating said plunger at a desired amplitude and frequency having said plunger movably mounted therein;

an oil chamber defined by said plunger and said vibration applying cylinder for pressurizing said plunger such that said plunger is capable of reciprocatory motion in said vibration applying cylinder;

an electromagnetic valve means for supplying hydraulic fluid to said plunger to reciprocate said plunger, said electromagnetic valve means being controlled so as to reciprocate said plunger at a desired frequency and amplitude;

hydraulic fluid passages communicating said electromagnetic valve means with said oil chamber;

a hydraulic power unit;

a hydraulic circuit means fluidly connecting said hydraulic power unit and said electromagnetic valve means;

a control unit means for actuating said hydraulic power unit to supply hydraulic fluid to said electromagnetic valve means through said hydraulic circuit and actuate and control said electromagnetic valve means to reciprocate said plunger at a desired frequency and amplitude in response to a control signal;

a controller for outputting a control signal to said control unit means, said control signal setting the desired frequency and amplitude of said plunger; and lifting means for lifting said vibration applying cylinder to a predetermined height.

2. The vibrator as set forth in claim 1, wherein:

said lifting means lifts said vibration applying cylinder to said predetermined height when said plunger is to be reciprocated and maintains said vibration applying plunger at said predetermined height; and said electromagnetic valve means causes said plunger to be displaced outwardly of said vibration applying cylinder approximately ½ of the total stroke of said plunger in said vibration applying cylinder after said lifting means has lifted said vibration applying cylinder to said predetermined height to bear the object at said upper portion of said plunger, whereby said plunger is subsequently reciprocated in said vibration applying cylinder.

3. The vibrator as set forth in claim 1, wherein said electromagnetic valve means comprises a single two position four port switch valve.

4. The vibrator as set forth in claim 1, wherein said hydraulic circuit means comprises a manual on/off switch valve for opening and closing said electromagnetic valve means, and said electromagnetic valve means is capable of reciprocating said plunger in said vibration applying cylinder at a relatively low frequency.

5. The vibrator as set forth in claim 1, wherein said plunger and said vibration applying cylinder define a second oil chamber for pressurizing the plunger;

said electromagnetic valve means comprises a first two position two port switch valve connected to said hydraulic circuit means for discharging hydraulic fluid from said oil chambers and a second two position two port switch valve connected to said hydraulic circuit means for feeding hydraulic fluid to said oil chambers, the hydraulic fluid being alternately fed to and discharged from said oil chambers by said electronic valve means.

6. The vibrator as set forth in claim 5, wherein:

said electromagnetic valve means has an excitation voltage of said switch valves; and a variable voltage control unit is operably connected to said electromagnetic valve means for varying the voltage to said switch valves to vary the opening and closing forces of said switch valves.

7. The vibrator as set forth in claim 1, wherein said plunger and said vibration applying cylinder define a second oil chamber for pressurizing said plunger such that said vibration applying cylinder is a double acting cylinder, the pressure receiving areas of said oil chambers being equal.

8. The vibrator as set forth in claim 1, wherein said lifting means comprises a single acting hydraulic cylinder connected to said hydraulic circuit means.

9. The vibrator as set forth in claim 1, wherein said lifting means comprises a pantograph jack.

10. The vibrator as set forth in claim 1, wherein said controller comprises a wireless remote control unit.

11. The vibrator as set forth in claim 1 or 4, wherein said controller comprises a first switch means for variably setting the frequency and amplitude of said plunger in said vibration applying cylinder and a second switch means for reciprocating said plunger in said vibration applying cylinder at a relatively low frequency.

12. The vibrator as set forth in claim 1, wherein said controller comprises a switch means for variably setting the frequency and amplitude of said plunger in said vibration applying cylinder and an indicator for indicating the frequency and amplitude thereon.

13. The vibrator as set forth in claim 1, wherein:

said control unit means comprises a control circuit electrically controlling said hydraulic power unit and said electromagnetic valve means; and a control box is provided having said control unit means and said hydraulic power unit therein.

14. The vibrator as set forth in claim 13, wherein said control box comprises at least an amplitude indicating portion and a frequency indicating portion.

15. The vibrator as set forth in claim 1, wherein said object is an automotive vehicle.

16. A vibrator, comprising:

a base plate for disposition on a test base;

a pair of lift cylinders operably mounted on said base plate, each said lift cylinder comprising a cylinder tube and a ram vertically movably accommodated therein, wherein each said ram is fixed to said base plate;

a movable plate, said cylinder tubes of said lift cylinders being fixed to said movable plate such that said movable plate is relatively movable with respect to said base plate;

a hydraulic power unit;

a hydraulic circuit means connected with said hydraulic power unit for feeding and discharging hydraulic fluid to and from said rams of said lift cylinders, said hydraulic circuit means comprising a switch valve for controlling the feed and discharge of hydraulic fluid to and from said rams of said lift cylinders;

a pair of support members fixed to said movable plate;

a vibration applying cylinder pivotably supported between said pair of support members;

an electromagnetic valve means connected to said hydraulic circuit means for feeding and discharging hydraulic fluid to and from said vibration applying cylinder;

control unit means for controlling said electromagnetic valve means and said hydraulic power unit;

a plunger vertically movably accommodated in said vibration applying cylinder for bearing the load of an object to be tested at an upper end portion thereof and being vertically movably responsive to the feed and discharge of hydraulic fluid to and from said vibration applying cylinder;

a position sensing means disposed on said vibration applying cylinder and comprising a guide tube movable with said plunger relative to said vibration applying cylinder for detecting the position of said plunger and providing a signal corresponding to the detected position to said control unit means, whereby said control unit means control said electromagnetic valve means in response to the detected position of said plunger;

a pair of roller brackets fixed to said base plate, each said roller bracket having a roller rotatably axially supported thereon; and an elongated handle having one end thereof fixed to said base plate.

17. The vibrator as set forth in claim 16, wherein:
said movable plate is a U-shaped member having a wide bending portion projecting forward of said base plate such that the vibrator can be turned to rest on said wide bending portion in an upright position.

18. The vibrator as set forth in claim 17, wherein said pair of support members are pivots fixed to said U-shaped member and rotatably connected with said vibration applying cylinder.

19. The vibrator as set forth in claim 16, wherein said base plate has a lower surface extending in a plane, and said rollers are disposed entirely above said plane.

20. The vibrator as set forth in claim 16, wherein said handle has a front end thereof connected to said base plate and a rear end thereof connected with said switch valve.

21. The vibrator as set forth in claim 16, wherein said movable plate has a pair of timing links connected thereto at one end of said timing links, the opposite ends of said timing links being pivotally axially supported by an inner side of said handle.

22. A vibrator, comprising:
a vibration applying cylinder having a plunger for reciprocal movement therein, said plunger having a spacer and a spacer attachment removably mounted to an upper end thereof for bearing the load of an object to be tested;

a hydraulic power unit;

a hydraulic circuit means connected with said hydraulic power unit for feeding and discharging hydraulic fluid to and from said vibration applying cylinder;

an electromagnetic valve means interposed between said hydraulic circuit and said vibration applying cylinder for feeding hydraulic fluid to said vibration applying cylinder for reciprocating said plunger at a desired amplitude and frequency; and lift means for lifting said vibration applying cylinder to a predetermined height.

23. The vibrator as set forth in claim 22, wherein said plunger has a cavity at said upper end thereof for removably receiving said spacer.

24. The vibrator as set forth in claim 22, wherein said spacer has a cavity therein at an upper end portion thereof for removably receiving said attachment therein for engagement with an object to be tested.

25. The vibrator as set forth in claim 22, wherein said attachment has an upper end portion having an engagement portion for engaging an object to be tested.

* * * * *